US011623049B2

(12) United States Patent
Pedersen

(10) Patent No.: US 11,623,049 B2
(45) Date of Patent: Apr. 11, 2023

(54) DOSE CAPTURING ASSEMBLY WITH SECONDARY IMAGE ANALYSIS FEATURE

(71) Applicant: Novo Nordisk A/S, Bagsvaerd (DK)

(72) Inventor: Bennie Peder Smiszek Pedersen, Haslev (DK)

(73) Assignee: Novo Nordisk A/S, Bagsvaerd (DK)

( * ) Notice: Subject to any disclaimer, the term of this patent is extended or adjusted under 35 U.S.C. 154(b) by 607 days.

(21) Appl. No.: 16/493,658

(22) PCT Filed: Mar. 14, 2018

(86) PCT No.: PCT/EP2018/056407
§ 371 (c)(1),
(2) Date: Sep. 12, 2019

(87) PCT Pub. No.: WO2018/167154
PCT Pub. Date: Sep. 20, 2018

(65) Prior Publication Data
US 2020/0129702 A1   Apr. 30, 2020

(30) Foreign Application Priority Data

Mar. 15, 2017 (EP) .................................... 17161025
Mar. 16, 2017 (EP) .................................... 17161242

(51) Int. Cl.
*A61M 5/315*       (2006.01)
*A61M 5/20*        (2006.01)
(Continued)

(52) U.S. Cl.
CPC ........ *A61M 5/3155* (2013.01); *A61M 5/2033* (2013.01); *A61M 5/2466* (2013.01);
(Continued)

(58) Field of Classification Search
CPC .............. A61M 5/2033; A61M 5/2466; A61M 5/3155; A61M 2205/6063
(Continued)

(56) References Cited

U.S. PATENT DOCUMENTS 7,292,797 B2    11/2007  Kunugi et al.
9,561,330 B2     2/2017  Draper et al.
(Continued)

FOREIGN PATENT DOCUMENTS

CN          1664713 A      9/2005
CN        103648555 A      3/2014
(Continued)

*Primary Examiner* — Bhisma Mehta
*Assistant Examiner* — Nidah Hussain
(74) *Attorney, Agent, or Firm* — Wesley Nicolas

(57) ABSTRACT

An add-on device for a drug delivery device comprises a camera for capturing an image of a scale drum, and a processor for determining the value of a captured image using a first image analysis process, the value corresponding to a set dose amount. If the determined value belongs to a pre-defined group of values, the determined value is confirmed using a second image analysis process in which for a given value from the pre-defined group of values one or more partial image areas and an associated nominal content thereof are pre-defined. If the captured content for each image area corresponds to the nominal content, the determined value is confirmed.

15 Claims, 7 Drawing Sheets

(51) Int. Cl.
*A61M 5/24* (2006.01)
*G06F 18/22* (2023.01)
*A61M 5/31* (2006.01)
*G06V 30/10* (2022.01)

(52) U.S. Cl.
CPC ......... *A61M 5/31585* (2013.01); *G06F 18/22* (2023.01); *A61M 2005/2407* (2013.01); *A61M 2005/3126* (2013.01); *A61M 2205/3306* (2013.01); *A61M 2205/50* (2013.01); *A61M 2205/6063* (2013.01); *A61M 2205/702* (2013.01); *G06V 30/10* (2022.01)

(58) Field of Classification Search
USPC .......................................................... 604/211
See application file for complete search history.

(56) References Cited

U.S. PATENT DOCUMENTS

| | | | |
|---|---|---|---|
| 10,820,872 B2 | 11/2020 | Van Nijnatten | |
| 2002/0120235 A1* | 8/2002 | Enggaard | A61M 5/20 604/135 |
| 2009/0318865 A1 | 12/2009 | Moller et al. | |
| 2013/0245604 A1 | 9/2013 | Kouyoumjian et al. | |
| 2013/0336555 A1 | 12/2013 | Baek et al. | |
| 2014/0194826 A1 | 7/2014 | Nielsen et al. | |
| 2016/0015902 A1* | 1/2016 | Draper | G06K 7/10881 604/207 |
| 2016/0082192 A1* | 3/2016 | Veasey | G16H 40/63 604/211 |
| 2017/0032211 A1 | 2/2017 | Allerdings et al. | |

FOREIGN PATENT DOCUMENTS

| | | |
|---|---|---|
| CN | 104869903 A | 8/2015 |
| CN | 104918648 A | 9/2015 |
| EP | 2646072 A1 | 10/2013 |
| EP | 2708253 A1 | 3/2014 |
| JP | 2003010327 A | 1/2003 |
| KR | 20130140301 A | 12/2013 |
| WO | 2006079918 A1 | 8/2006 |
| WO | 2010052275 A2 | 5/2010 |
| WO | 2014161952 A1 | 10/2014 |
| WO | 2015110520 A1 | 7/2015 |
| WO | 2016001298 A1 | 1/2016 |
| WO | 2016062604 A1 | 4/2016 |
| WO | 2016113127 A1 | 7/2016 |

* cited by examiner

DOSE CAPTURING ASSEMBLY WITH SECONDARY IMAGE ANALYSIS FEATURE

CROSS-REFERENCE TO RELATED APPLICATIONS

This application is a 35 U.S.C. § 371 National Stage application of International Application PCT/EP2018/056407 (published as WO 2018/167154), filed Mar. 14, 2018, which claims priority to European Patent Applications 17161025.6, filed Mar. 15, 2017, and 17161242.6, filed Mar. 16, 2017, the contents of all above-named applications are incorporated herein by reference.

The present invention generally relates to medical devices and assemblies for which the generation, collecting and storing of data are relevant. In specific embodiments the invention relates to devices and systems for capturing and organizing drug delivery dose data in a reliable and cost-effective way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices being either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2015/110520 describes an electronic supplementary device (or "add-on module") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialled into the drug delivery device. To improve reliability of the OCR process two OCR algorithms intended to have the same output may be operated in parallel. They both perform similar steps however the individual methods used in each step may vary. A further external device for a pen device is shown in WO 2014/161952. Further examples of devices using optical dose determination based on information provided on a scale drum is disclosed in US 2016/0015902, US 2017/0032211 and EP 2 708 253.

Having regard to the above, it is an object of the present invention to provide assemblies, devices and methods allowing reliable and cost-effective operation and manufacturing of a drug delivery assembly comprising a dose capturing functionality.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first general aspect of the invention a dose capturing assembly adapted to be releasably attached to or formed integrally with a drug delivery device is provided, the drug delivery device comprising a housing, a drug reservoir or means for receiving a drug reservoir, drug expelling means comprising a rotatable dose setting member allowing a user to set a dose amount of drug to be expelled, an actuation member actuatable between a first and a second state, the first state allowing a dose amount to be set, the second state allowing the drug expelling means to expel a set dose, and an indicator with indicia adapted to display the set dose amount during dose setting, and to display the remaining dose amount to be expelled during drug expelling. The dose capturing assembly comprises a camera adapted to capture an indicia-containing image of the indicator (i.e. an image of a portion of the indicator), and processor means adapted to determine the value of a captured image using a first image analysis process, the value corresponding to the set dose amount, and, if the determined value belongs to a pre-defined group of values, then confirm the determined value based on a second image analysis process. For a given value from the pre-defined group of values one or more partial image areas and an associated nominal content thereof are predefined, each nominal content being different from the value of a captured image using the first image analysis process. The second image analysis process comprises the steps of: for a given value from the pre-defined group of values compare the captured content of the partial image areas with the nominal content, and, if the captured content corresponds to the nominal content, then confirm the determined value based on the second image analysis process.

In this way image features of a given location can be chosen solely in order to be able to discriminate between values which have been found to be mixed-up by the given primary image process utilized. In this way a secondary image process is utilized only when needed, this in contrast to a process in which every value is the target of a secondary "validating" image process.

The first image analysis process may be in the form of template matching and the determined value is a rotational position of the indicator member. Alternatively, the first image analysis process may be an OCR process and the determined value is a numerical value corresponding to a rotational position of the indicator member.

For a given position the nominal content of the corresponding partial image areas may be either "universally" distinctive or "relatively" distinctive for a given number of positions. The result of the secondary image process may be utilized to "negatively" determine that the result of the primary image process is incorrect and thus result in an error message, or it may be utilized to "positively" determine that the result of the primary image process is one of two alternatives.

In an exemplary embodiment the dose capturing assembly further comprises an electronically controlled display adapted to display a set dose amount, wherein the processor means is adapted to control the display to show a confirmed value, and control the display to show an error indication if the determined value is not confirmed. The processor means may be adapted to determine an expelled dose amount based at least in part on confirmed values.

In a further exemplary embodiment the dose capturing assembly additionally comprises a sensor assembly adapted to detect rotational movement of the dose setting member, the processor means being adapted to determine if the determined value belongs to a second pre-defined group of values (see below), and if the determined value belongs to the second pre-defined group of values, then turn the display into an operating state.

The dose capturing assembly may be in the form of an add-on logging device adapted to be releasably attached to a drug delivery device is provided, the drug delivery device comprising a housing, a drug reservoir or means for receiving a drug reservoir, drug expelling means comprising a rotatable dose setting member allowing a user to set a dose amount of drug to be expelled, an actuation member actuatable between a first and a second state, the first state allowing a dose amount to be set, the second state allowing the drug expelling means to expel a set dose, and an indicator adapted to display the set dose amount during dose setting, and to display the remaining dose amount to be expelled during drug expelling.

The add-on logging device may be provided in combination with a drug delivery device comprising a housing, a drug reservoir or means for receiving a drug reservoir, drug expelling means comprising a rotatable dose setting member allowing a user to set a dose amount of drug to be expelled, an actuation member actuatable between a first and a second state, the first state allowing a dose amount to be set, the second state allowing the drug expelling means to expel a set dose, and an indicator adapted to display the set dose amount during dose setting, and to display the remaining dose amount to be expelled during drug expelling.

The drug expelling means may further comprise a piston rod adapted to engage and axially displace a piston in a loaded cartridge in a distal direction to thereby expel a dose of drug from the cartridge, a rotatable drive member, and a drive spring coupled to the drive member, the dose setting member allowing a user to simultaneously set a dose amount to be expelled and strain the drive spring correspondingly by rotation of the drive member to a set position, wherein the strained drive spring is released to rotate the drive member to expel the set dose amount when the actuation member is actuated from the first to the second state.

The dose capturing assembly may be formed integrally with a drug delivery device comprising a housing, a drug reservoir or means for receiving a drug reservoir, drug expelling means comprising a rotatable dose setting member allowing a user to set a dose amount of drug to be expelled, an actuation member actuatable between a first and a second state, the first state allowing a dose amount to be set, the second state allowing the drug expelling means to expel a set dose, and an indicator adapted to display the set dose amount during dose setting, and to display the remaining dose amount to be expelled during drug expelling.

The indicator may be in the form of a tubular indicator member having an outer surface and being adapted to rotate relative to the housing during dose setting and dose expelling corresponding to an axis of rotation, the amount of rotation corresponding to a set dose respectively the amount of drug remaining to be expelled from a reservoir by the expelling means, the indicator member having an initial rotational position corresponding to no dose amount being set, a pattern being arranged circumferentially or helically on the indicator member outer surface and comprising a plurality of indicia, the currently observable indicia indicating to a user the size of a currently set dose amount of drug to be expelled, and the housing comprises a window allowing a user to observe a portion of the indicator member. The dose capturing assembly may be adapted to capture an image of the indicia.

The tubular indicator member may comprise a second surface pattern being arranged circumferentially or helically on the indicator member inner or outer surface and comprising a plurality of code structures, the dose capturing assembly being adapted to capture an image of the code structure. For example, the code structure may be formed on the same surface portion as the indicia visible to a user but with non-visible printing.

In a further aspect of the invention a dose capturing assembly adapted to be releasably attached to or formed integrally with a drug delivery device is provided, the drug delivery device comprising a housing, a drug reservoir or means for receiving a drug reservoir, drug expelting means comprising a rotatable dose setting member allowing a user to set a dose amount of drug to be expelled, an actuation member actuatable between a first and a second state, the first state allowing a dose amount to be set, the second state allowing the drug expelling means to expel a set dose, and an indicator adapted to display the set dose amount during dose setting, and to display the remaining dose amount to be expelled during drug expelling. The dose capturing assembly comprises an electronically controlled display adapted to display a set dose amount, a sensor assembly adapted to detect rotational movement of the dose setting member, and a camera adapted to capture an image of the indicator. The logging assembly further comprises processor means adapted to determine the value of a captured image, the value corresponding to the set dose amount, determine if the determined value belongs to a pre-defined group of values, and, if the determined value belongs to the pre-defined group of values, then turn the display into an operating state.

The dose capturing assembly may be in the form of an add-on logging device adapted to be releasably attached to a drug delivery device as described above. The add-on logging device may be provided in combination with such a drug delivery device.

The predefined group of values may for example comprise one-digit values such a 0, 2 and 4 for which image characteristic will be highly unique compared to positions like for example 66, 68, 80 and 88 which would then not be comprised in the predefined group.

The processor means may be adapted to control the display dynamically to show the set dose amount based on input from the sensor assembly, and determine an expelled dose amount based at least in part on input from the camera. The processor means may be adapted to calibrate the rotational position of the sensor assembly corresponding to a determined value belonging to the pre-defined group of values.

The determined value may be a rotational position of the indicator member determined by template matching, or alternatively a numerical value determined by an OCR process, the numerical value corresponding to a rotational position of the indicator member.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as noninsulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

Figure 1A:
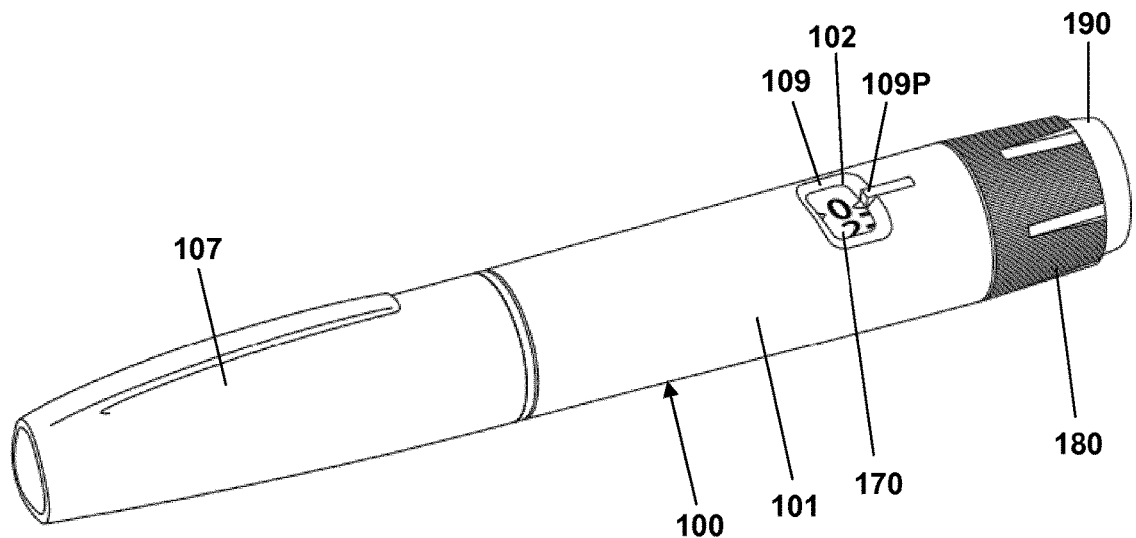
FIG. 1A shows a pen-formed drug delivery device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a prefilled drug delivery will be described, such a device providing the basis for the exemplary embodiments of the present invention. Although the pen-formed drug delivery device 100 shown in FIGS. 1-3 may represent a "generic" drug delivery device, the actually shown device is a FlexTouch® prefilled drug delivery pen as manufactured and sold by Novo Nordisk A/S, Bagsvrd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. The window is in the form of an opening in the housing surrounded by a chamfered edge portion 109 and a dose pointer 109P, the window allowing a portion of a helically rotatable indicator member 170 (scale drum) to be observed. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
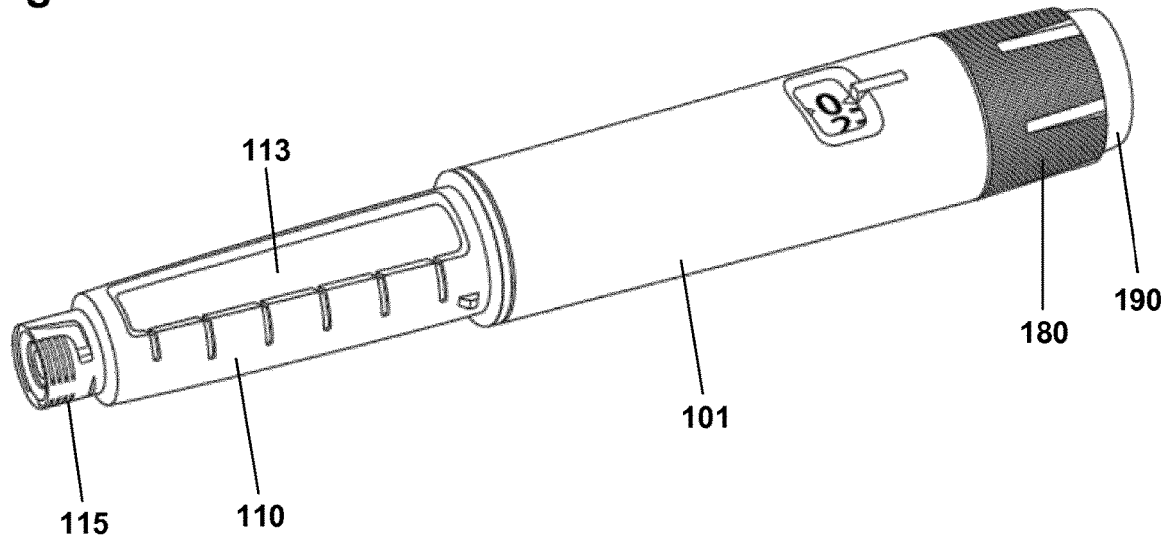
FIG. 1B shows the pen device of FIG. 1A with the pen cap removed.

Although FIG. 1 shows a drug delivery device of the prefilled type, i.e. it is supplied with a premounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to electronic circuitry adapted to interact with a drug delivery device, an exemplary embodiment of such a device will be described for better understanding of the invention.

Figure 2:
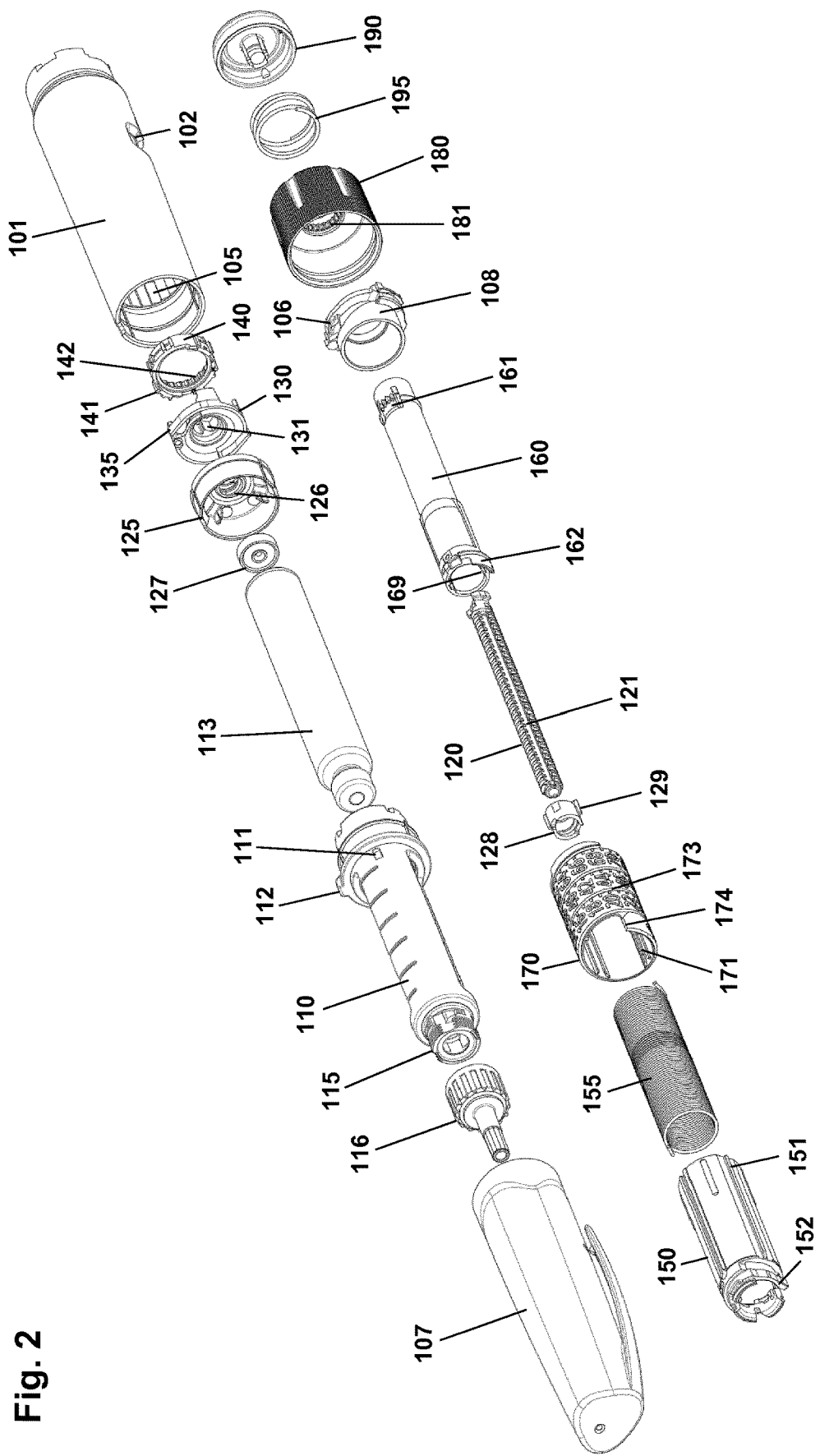
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasable mounted, proximal coupling means in the form of two opposed protrusions 111 allowing a cap 107 to be releasable mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves 121 and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 3B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

The dial system comprises a ratchet tube 150, a reset tube 160, a scale drum 170 with an outer helically arranged pattern forming a row of dose indicia, a user-operated dial member 180 for setting a dose of drug to be expelled, a release button 190 and a torque spring 155 (see FIG. 3). The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
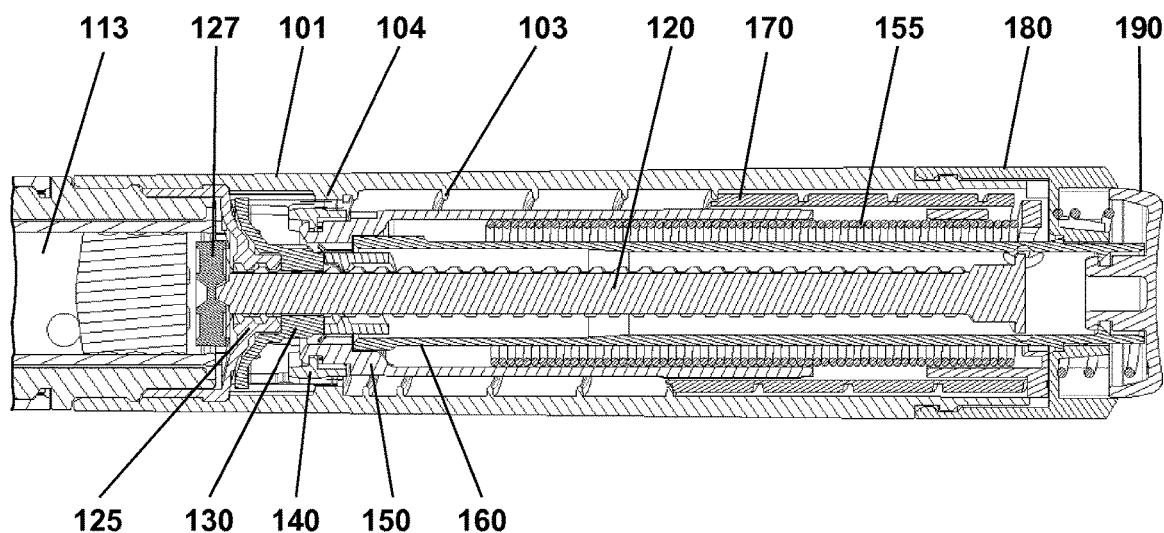

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it. As the ratchet tube is connected to the distal end of the torque spring 155, the spring is loaded. During dose setting, the arm 152 of the ratchet performs a dial click for each unit dialled due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
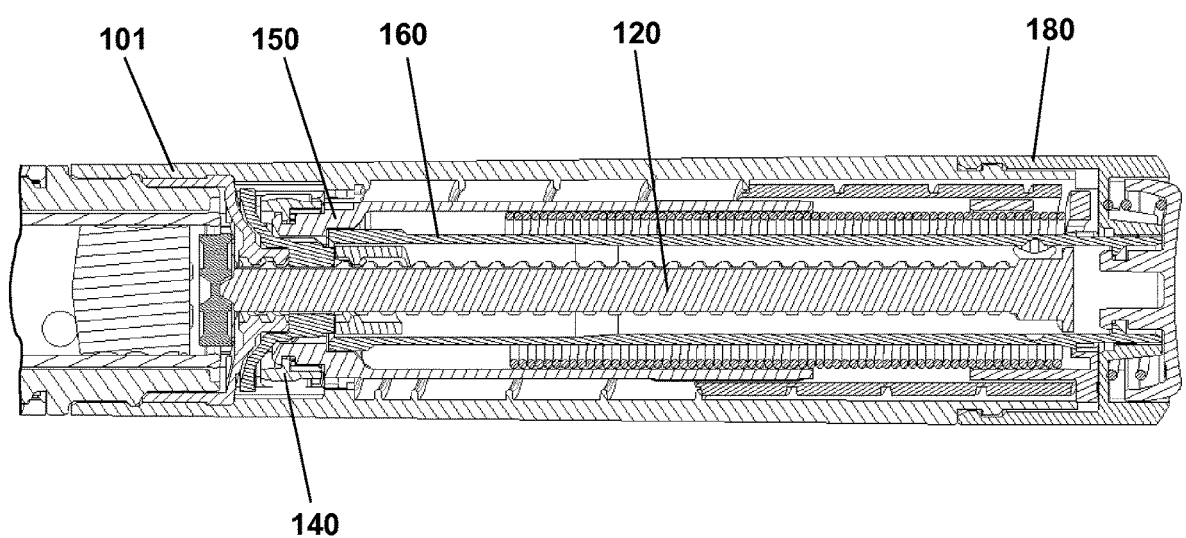

To deliver a set dose, the push button 190 is pushed in the distal direction by the user as shown in FIG. 3B. The reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialling mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 181 engaging a number of corresponding teeth arranged on a flexible carrier portion 161 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, exemplary embodiments of an add-on logging device will be described, the embodiments serving as a platform for implementing aspects of the present invention.

Figure 4:
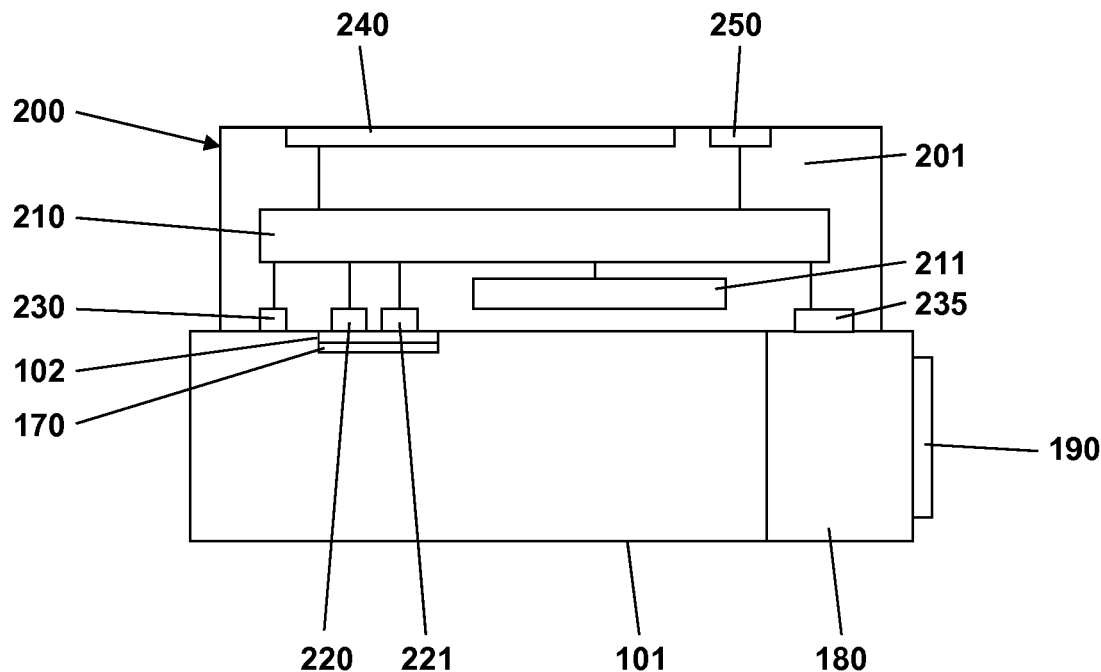
FIG. 4 shows a schematic representation of an add-on device.

FIG. 4 shows a schematic representation of an add-on device 200 in a state where it has been mounted on the housing 101 of a drug delivery device 100 of the above-described pen type. The add-on device is adapted to determine the amount of drug expelled from the drug delivery device during an expelling event, i.e. the subcutaneous injection of a dose of drug. In the shown embodiment determination of an expelled dose of drug is based on determination of scale drum position at the beginning and at the end of the expelling event. To determine the rotational position of the scale drum the dose numerals as seen in the display window 102 may be captured and used. Actual determination of scale drum position may be performed using e.g. template matching (see below) or optical character recognition (OCR). Alternatively a dedicated code pattern may be provided on the scale drum as disclosed in e.g. WO 2013/004843.

The add-on device comprises a housing 201 in which is arranged electronic circuitry 210 powered by an energy source 211. The electronic circuitry is connected to and interacts with a light source 220 adapted to illuminate at least a portion of the scale drum 170 seen in the window 102, an image capture device (camera) 221 adapted to capture image data from the scale drum, a mounting switch 230 adapted to engage the pen housing 101, a display 240 and user input means in the form of one or more buttons 250. In the shown embodiment a further activity switch 235 adapted to engage the dose setting member 180 is provided. Alternatively or in addition an acoustic sensor may be provided to detect specific sounds generated by the expelling mechanism during dose setting and dose expelling. The electronic circuitry 210 will typically comprise controller means, e.g. in the form of a generic microprocessor or an ASIC, ROM and RAM memory providing storage for imbedded program code and data, a display controller and a wireless transmitter/receiver.

The add-on device further comprises mounting means (not shown) adapted to releasably mount and securely hold and position the add-on device on the pen housing. For the shown embodiment the add-on device covers the display window for which reason the current dose size shown in the display window has to be captured and displayed on the electronic "virtual" display 240. Alternatively, the add-on device may be designed to allow the user to view the display window.

The coupling means may be in the form of e.g. a bore allowing the add-on device to slide in place on the pen body, flexible gripping structures allowing the add-on device to be mounted in a perpendicular direction, locking means that will snap in place when the add-on device is mounted on the pen body, or locking means which has to be operated by the user, e.g. a hinged latch member or a sliding member.

Figure 5:
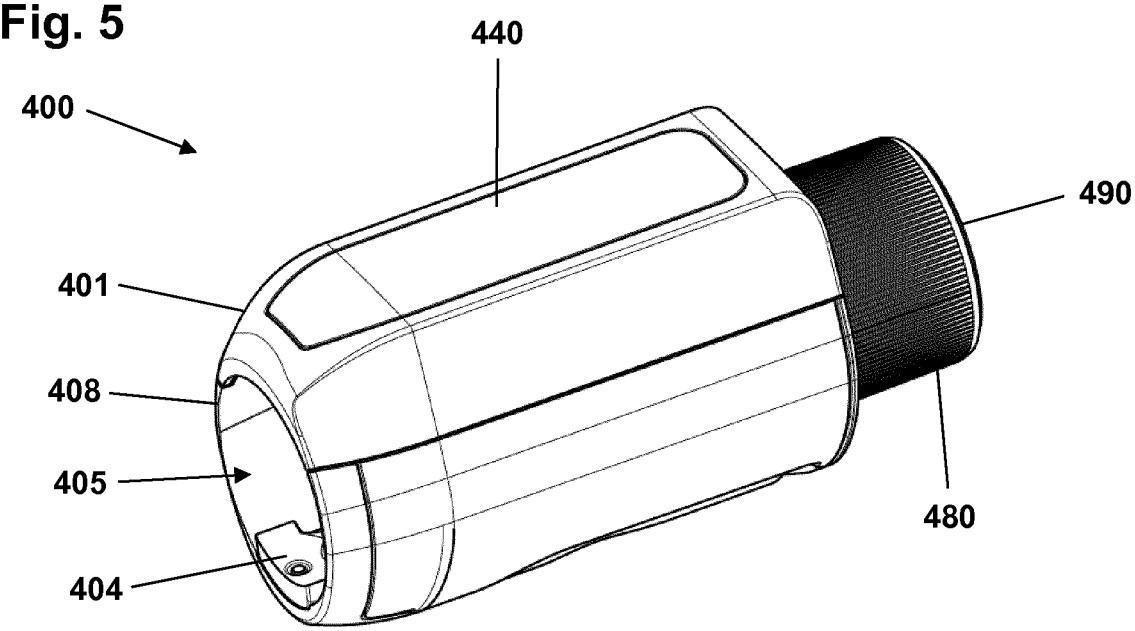
FIG. 5 shows an add-on device mounted on the housing of a drug delivery device.

FIG. 5 shows a further embodiment of an add-on module 400, the module comprising a housing 401, a display window 440, and proximally arranged user accessible add-on dial member 480 and user accessible add-on release button 490, the latter being adapted to cover and cooperate with the corresponding structures on the drug delivery device on which the add-on module is mounted. Such an add-on module is described in greater detail in EP 16171883.8.

Providing a virtual display for an add-on accessory device which covers the scale drum window during operation results in a higher degree of complexity just as the required additional display adds to the size and cost of the device. Further, although it may be possible to provide a virtual display which is accurate and reliable to a very high degree, users may be concerned that this is not always the case. Correspondingly, EP 16196559.5 describes an add-on module in which a camera via an optical arrangement is arranged to capture images of the scale drum, the user at the same time being able via a transparent housing window to directly observe the scale drum during dose setting.

In the above-described add-on devices scale drum position may be determined by template-matching with a stored representation of the entire scale drum surface image.

Figure 6:
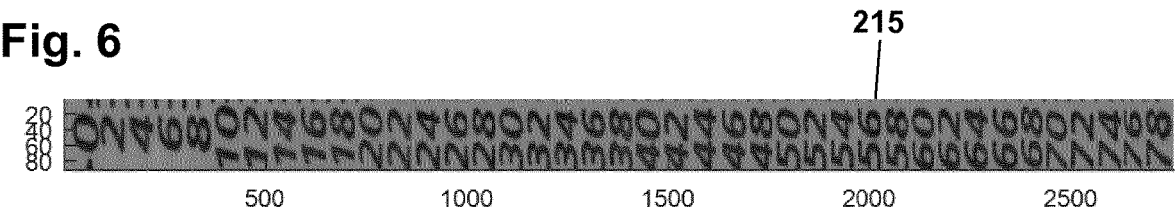
FIG. 6 shows a scale drum reference representation.
Figure 7:
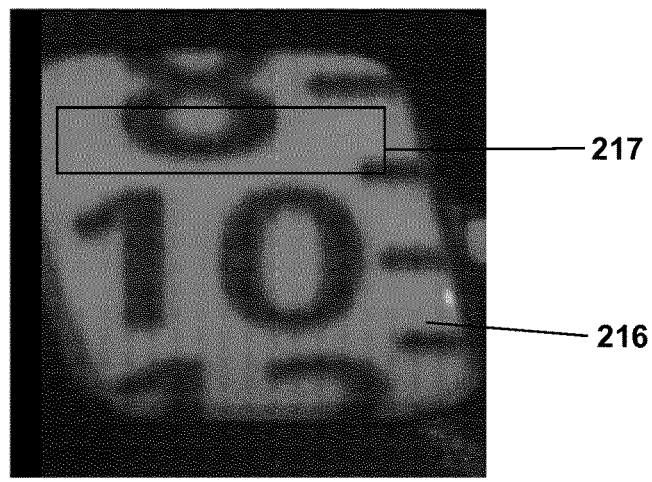
FIG. 7 shows an image capture from a scale drum.
Figure 8:
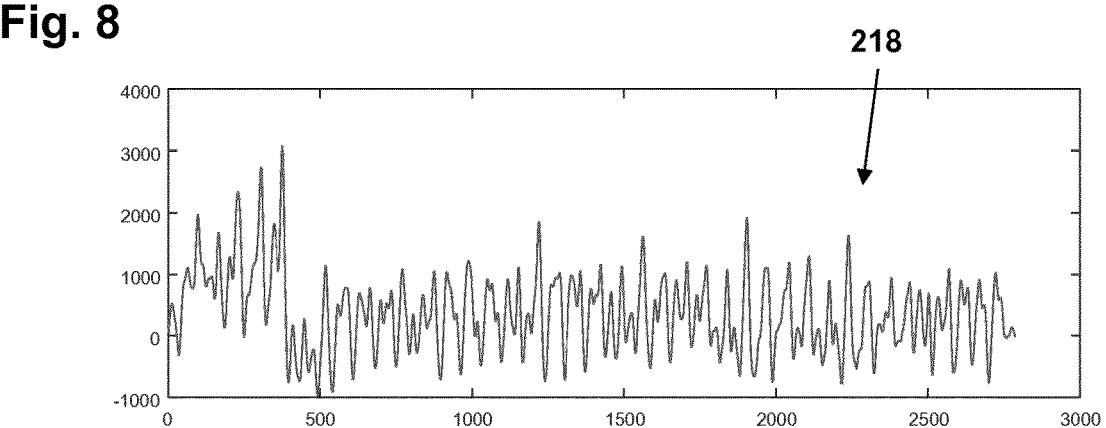
FIG. 8 shows cross correlation of the FIG. 7 image portion to the reference representation.
Figure 9:
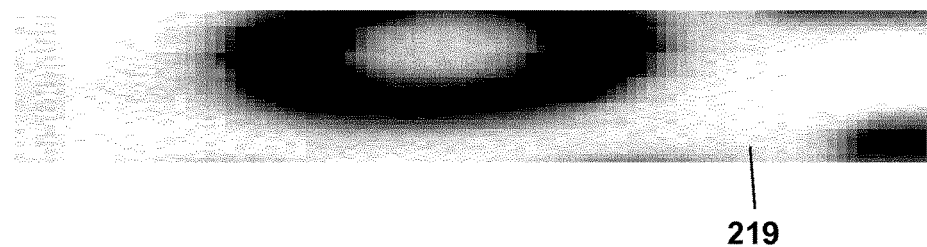
FIG. 9 shows a matched portion of the reference representation.

Correspondingly, FIG. 6 illustrates a template image 215 of the whole scale-drum. The image has been obtained by concatenating parts of successive images from a film where the scale-drum moves from position 80 to position 0. More specifically, the template has been made by concatenating the vertical centre of each frame in the movie, automatically creating a sheared image, this resulting in all digits being tilted as can be seen when compared to the scale drum digits shown in FIG. 7. Alternatively, the ribbon image could be obtained from a CAD-drawing of the scale drum print for a FlexTouch® device, the drawing being cut and sheared to produce a long ribbon. The template image is used as a reference when to determine the position of a specific image. The pixel position (horizontal axis in the above figure) corresponds to the drum position (in degrees, IU or other units). As an example, FIG. 7 shows an image 216 of the scale-drum window where the position corresponds to 10 IU, the rectangle 217 illustrating the area that is used for position detection. FIG. 8 then shows the cross correlation of the rectangle image portion to the reference 115 as a function 118 of pixel position. Searching for the peak reveals a best match at pixel position 341, corresponding to the cut 119 from the reference image as shown in FIG. 9. The reference image at this pixel offset was taken when the scale drum was in a position 9.8 IU. Indeed, if the template image has been created by sheering the digits this also means that the image taken with the camera should be sheered correspondingly before matching with the template.

In general, the captured image should be processed to correspond to the stored template, or, alternatively, the template image should be processed to correspond to the captured images before being stored. More specifically, in addition to the above-described shearing issue, the captured images may be distorted due to e.g. the angular orientation between the camera and the scale drum and the influence of any optical elements arranged in front of the camera.

Correspondingly, the template image may be processed before storage to create a "distorted" image which matches the images as actually captured.

Irrespective of how scale drum position is determined, be it by template matching or OCR, the utilized method may give rise to incorrect results, typically when two images or characters are very similar. Addressing this issue, the present invention provides a camera-based system in which a primary image position determination, e.g. template matching or OCR, is used in combination with a secondary image control process which selectively controls the result of the primary image process.

The present invention is based on realizing that for a given method of scale drum position determination, e.g. template matching or OCR, some positions or values will be determined with a higher degree of reliability. Correspondingly, in a preferred embodiment the secondary image control process of the present invention provides that for such positions or values a second analysis will take place. However, in contrast to merely performing a second similar test, e.g. another OCR process, the image in question is analysed to determine image features which effectively can be used to determine whether or not the primary image process analysis is correct or not.

More specifically, for a given position or value the corresponding image is initially analysed for image features which are either "universally" distinctive, e.g. a pair of opposed arrows as used in combination with the "0" on the scale drum, or which are "relatively" distinctive for a given number of "problem" positions which have been shown to result in "mixed up" results, e.g. "10" may be confused with "18" or "20" may be confused with "30".

For each relevant "problem" position the identified one or more distinctive features are characterized by a given location and a given nominal content. In a simple set-up for a white scale drum with black indicia each location, i.e. a partial image portion or area, may be characterized by a grey scale value ranging from "all white" over grey values to "all black". The position, size and form of each partial image portion may be chosen individually for each relevant position of the scale drum.

As indicated above the "relative distinctiveness" for the image features of a given location should be chosen solely in order to be able to discriminate between positions which have been found to be mixed-up by the given primary image process utilized. Ideally, image portions (or areas) should be identified which for the scale drum position in question have as distinct as possible content, e.g. "fully white" or "fully black".

For example, if for the given primary image process utilized it has been shown that "10" may be confused with "18", a chosen partial image portion may correspond to the centre of the second numeral which for "10" would be dominantly white whereas for "18" it would be dominantly black. As a second partial image portion the entire area of the second numeral may be chosen, which for "0" on average would be lighter grey than "8".

Depending on the intended outcome of the combined primary and secondary image processes, the result of the secondary image process may be utilized to "negatively" determine that the result of the primary image process is incorrect and thus result in an error message, or it may be utilized to "positively" determine that the result of the primary image process is e.g. "10" instead of "18".

Figure 10:
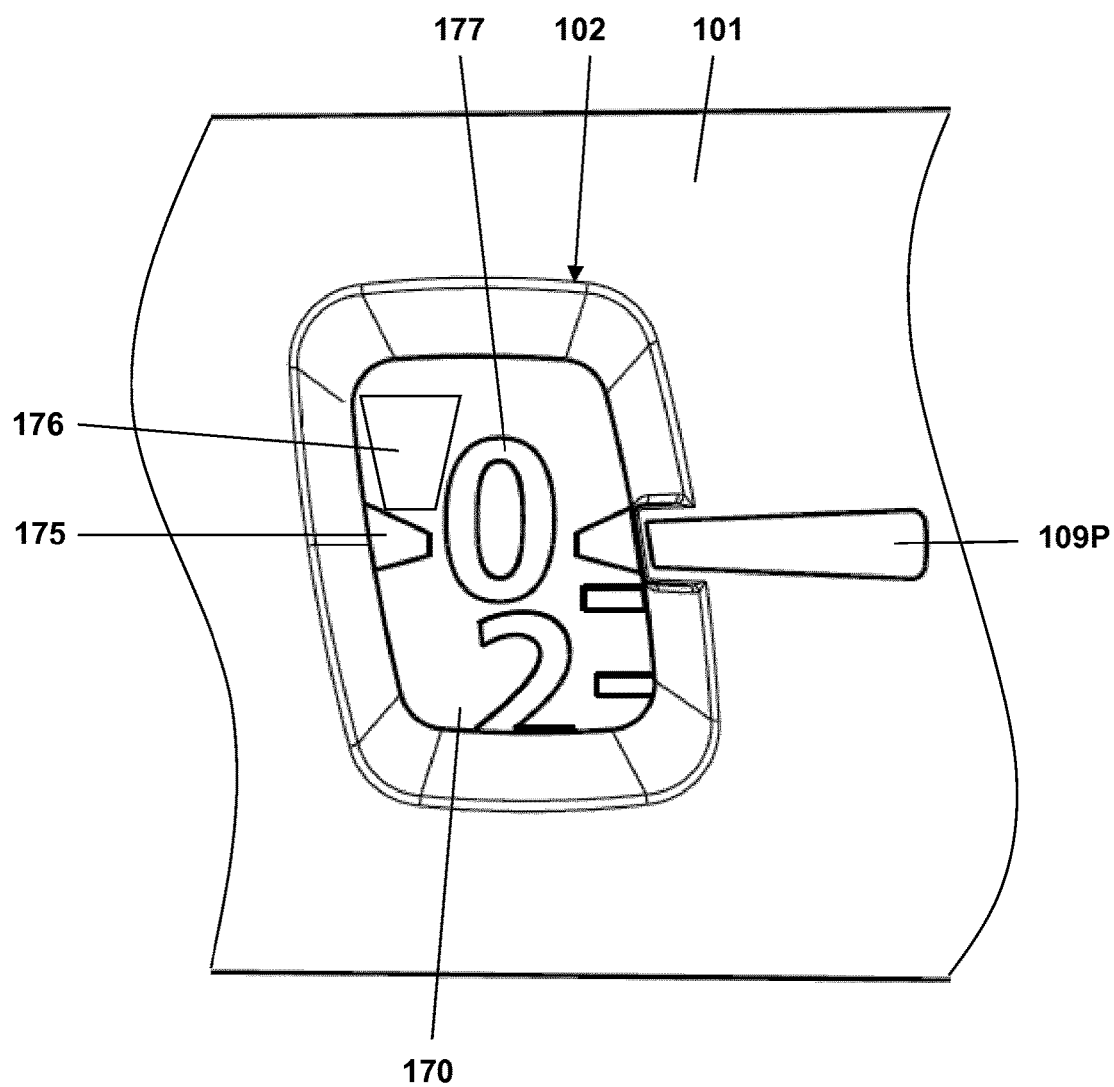
FIG. 10 shows a scale drum in an initial position with secondary image portions identified.

As an example of a "universally distinctive" feature reference is made to FIG. 10, showing the scale drum 170 positioned corresponding to the initial zero position with the numeral (or indicia) "0" 177 arranged next to the housing pointer 109P showing in the housing window 102. For this position each of the arrow image portions 175 as well as each of the two upper relatively large white triangular areas 176 would be distinctive. As above, the universally distinctive feature may be used to provide a negative or a positive outcome of the combined processes.

Figure 11:
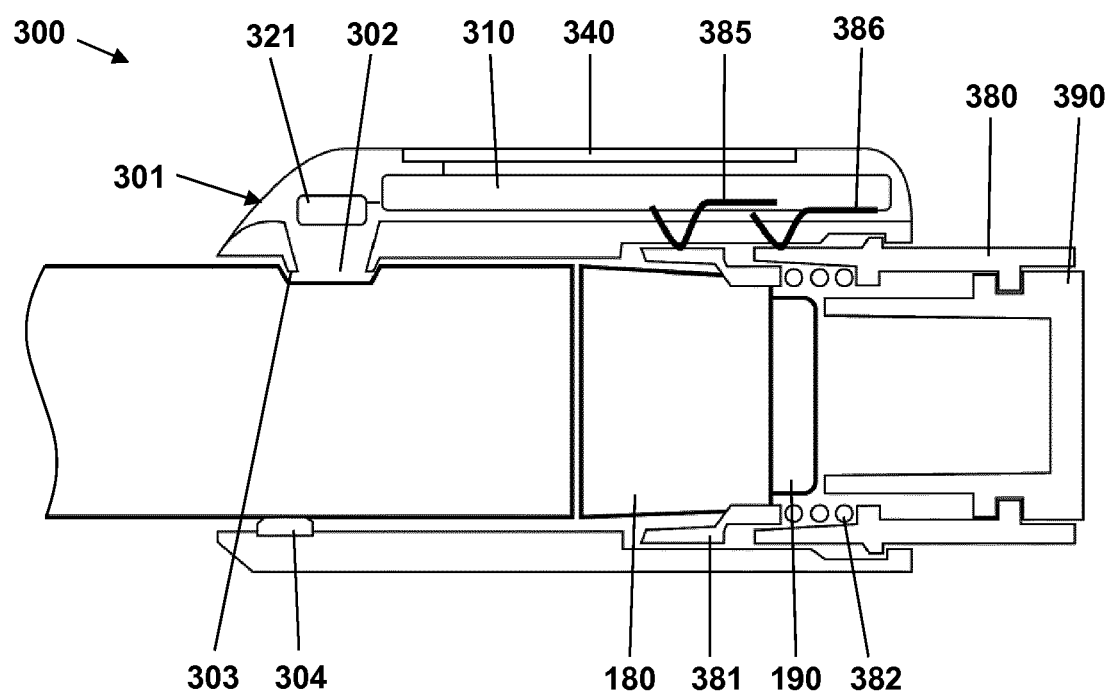
FIG. 11 shows a schematic representation of a further add-on device.

Turning to FIG. 11 a further embodiment of an add-on module 300 is shown, the module comprising a position sensor assembly in combination with a state switch actuated by a release member provided as part of the module. More specifically, the add-on module 300 comprises a housing 301 in which are arranged electronic circuitry 310, an energy source, a light source, a camera device 321 and a display 340, this generally corresponding to the components of the add-on module shown in FIG. 4. The add-on module housing forms a bore adapted to receive the generally cylindrical proximal portion of the pen device, the bore being defined by a generally cylindrical mounting surface adapted to face the pen device. A camera opening 302 is formed in the mounting surface. A small clearance is provided between the bore and the pen to allow the pen to be received in the bore. A firm grip between the two structures is provided by a locking structure 304 on the add-on module adapted to engage the pen device and securing a firm grip. The locking structure may be spring biased and adapted to snap in place when the add-on module is mounted on the pen. Alternatively the locking structure may be in the form of a user-operated lock. The add-on module comprises a positioning structure 303 protruding from the mounting surface and being adapted to engage at least portions of the opening edge to thereby position the add-on module both axially and rotationally relative to the opening. In the shown embodiment the positioning structure is in the form of a protruding lip 303 structure surrounding at least partially the camera opening, the lip structure being adapted to form-fitting engage the edge portion of the window opening to thereby ensure correct positioning both axially and rotationally between the two housing structures and thereby between the camera device and the scale drum.

Additionally, the add-on module 300 is provided with a user accessible add-on dial member 380, a user accessible add-on release button 390, a position sensor assembly comprising a cylindrical code member 381 in combination with a code contact array 385, and a state switch 386 associated with the add-on dial member. In the shown embodiment the mounting switch functionality is integrated in the position sensor assembly, see below. In the shown embodiment the add-on dial member 380 and the add-on release button 390 is mounted axially locked to each other to form a combined add-on dial and release member. The two members may also be rotationally locked to each other. As appears, when the add-on module is mounted on the pen device the pen dose setting member and the pen release button are covered by the add-on module.

The cylindrical code member 381 has an inner surface adapted to axially engage the dose setting member 180 when the add-on device is mounted on the pen device, the mating surfaces providing non-rotational engagement, e.g. based on the axially oriented groove pattern provided on the Flex-Touch® pen device as shown in FIG. 1A. The add-on dial member 380 is coupled freely rotatable to the module housing 301 but is in non-rotational engagement with the code member 381 and thus the dose setting member 180 when the add-on module is mounted on the pen device. The add-on dial member 380 is arranged to be moved axially relative to the module housing between an initial proximal-most position and an actuated distal-most position. A bias spring 382 is provided between the code member 381 and the add-on dial member 380 to ensure that the combined add-on member is biased towards its proximal-most position. The add-on release button portion 390 of the combined add-on member is adapted to engage the pen device release button 190 when moved axially relative to the module housing. In this way a dose is set by means of the add-on dial member portion 380 and a set dose is released by means of the add-on release button portion 390.

The position sensor assembly comprises the above-described generally cylindrical code member having an outer circumferential surface provided with a Gray code pattern rotating together with the add-on dial member 380, and a contact assembly comprising a number of galvanic contact members in sliding engagement with the code pattern surface. The output from the position sensor assembly is decoded by the processor and a rotational position is determined which is then used to control the display. The position sensor may be "absolute" having a resolution corresponding to the number of increments for a full rotation of the dose setting member, e.g. 24 increments, or a fraction thereof, e.g. 8 increments. As the dose setting member in most pens is designed to rotate more than a full rotation, e.g. corresponding to 80 increments, the electronics would in both cases have to add increments after having reached the maximum resolution of e.g. 8 or 24 increments. As the display control thus is based on position determination instead of counting as described above, the system is more robust to skipping an input, e.g. during wake-up or if the user rotates the dose setting member very fast.

In addition to the position sensing feature the Gray code arrangement also provides a motion sensing feature, i.e. as long as the detected values changes within a given amount of time a dose can be assumed to be set.

In addition to the position and motion sensing features the Gray code arrangement also provides a wake-up switch arrangement having a low-power sleep mode yet provides a wake-up signal when the code member is rotated during initial dose setting. As the code member inevitably will move during mounting of the add-on module, the Gray code arrangement may also provide a mounting switch which will wake-up the electronics during mounting.

In the shown embodiment the state switch assembly comprises one or more contact members 386 in sliding engagement with the distal portion of the add-on dial member 380 on which a circumferential code ring is arranged, this providing a switch arranged to detect axial movement of the add-on release button 390 between a proximal dose setting state and a distal dose release state. The contact members of both the position sensor and the state switch may be in the form of flexible contact arms which may be provided in the form a combined contact arm array.

In an alternative embodiment (not shown) the axial state switch may be integrated in the position sensor by utilizing the Gray code surface and the contact assembly. More specifically, the cylindrical code member may be arranged to move axially between a proximal position corresponding to a dose setting state and a distal position corresponding to a dose release state, the code member being moved axially by means of the add-on release button. A similar sensor arrangement is disclosed in WO 2010/052275 which is hereby incorporated by reference.

As described above, the position sensor will in most cases not be absolute, for which reason the actual position of the scale drum as shown on the display will have to be based on an initial value determined by other means, i.e. the image capture. In the following two examples of this concept is described.

In a preferred embodiment the add-module is provided with a memory in which the last rotational position of the scale drum determined by use of the camera is stored. When the add-on module is mounted on a new pen device the memory has to be reset, however, to avoid that the user will have to perform certain operations as part of the initial mounting procedure (as was the case for the FIG. 4 embodiment described above), the add-on module may be provided with an automatic scale drum position capture. More specifically, when it is detected by the mounting switch means that the add-on module has been mounted anew (or for the first time) on a pen device, the camera will capture an image of the scale drum which will be processed to determine the position of the scale drum, e.g. by template matching, and stored in the "last-position" memory. The position can then also be used to display the corresponding current scale drum dose size value on the module display.

Alternatively, displayed values may be based on an image captured initially during a dose setting event, the image being used to determine an initial scale drum position on which the display showing is based during dose setting. The initial image capture may be prompted by e.g. the user (lightly) pressing the release button or an image may be captured "on the fly" after movement of the dial member has been detected.

In both of these scenarios it is important that the initial dose setting position is correctly determined as otherwise the user would experience that the dose dialled and shown on the display will not correspond to the true position determined at the end of dose setting, i.e. it may be acceptable that a dialled dose of 25 units is corrected to a true value of 26 (which may then be dialled back to 25), however, it may be less acceptable that a dialled dose of 25 units is corrected to a true value of 30.

Addressing this issue, in a second aspect of the present invention a method of assuring that an initially captured scale drum position (or value) is correct is provided. More specifically, when the scale drum is dialled to positions like for example 0, 2, 4 the image characteristic will be highly unique compared to positions like for example 66, 68, 80 and 88. Correspondingly, a system is provided wherein the display is turned into an operating state only when determined positions belong to a pre-defined group of values.

In case the user starts to set a dose and the display dose not turn on, the user will have been instructed to slowly rotate the dial member until the display turns on. Indeed, for the concept to be attractive the user should experience that the display turns on as expected in most cases, however, as the dial member in most use scenarios will have been parked in the initial zero position, and perhaps unintentionally has been rotated a few units, it is believed that dose setting in most cases will begin with the scale drum at or close to the initial zero position, this allowing the scale drum position to be reliably determined by initial image capture and position determination.

In the above description of exemplary embodiments of the invention, the image capturing concepts of the invention has been described for use in add-on dose logging devices adapted to be releasably mounted on a drug delivery device, however, the disclosed concepts may with the same effect be utilized in image capturing circuitry incorporated in drug delivery devices comprising a corresponding indicator.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A dose capturing assembly adapted to be releasably attached to or formed integrally with a drug delivery device, the drug delivery device comprising:
   a housing,
   a drug reservoir or structure for receiving a drug reservoir,
   drug expelling structure comprising a rotatable dose setting member allowing a user to set a dose amount of drug to be expelled,
   an actuation member actuatable between a first and a second state, the first state allowing a dose amount to be set, the second state allowing the drug expelling structure to expel a set dose, and
   an indicator with indicia adapted to display the set dose amount during dose setting, and to display the remaining dose amount to be expelled during drug expelling,
   the dose capturing assembly comprising:
   a camera adapted to capture an indicia-containing image of the indicator, and processor structure adapted to:
(a) determine the value of a captured image using a first image analysis process, the value corresponding to the set dose amount, and
(b) if the determined value belongs to a pre-defined group of values, then confirm the determined value based on a second image analysis process,
wherein for a given value from the pre-defined group of values one or more partial image areas and an associated nominal content thereof are pre-defined, each nominal content being different from the value of a captured image using the first image analysis process, the second image analysis process comprising the steps of:
(i) for a given value from the pre-defined group of values compare the captured content of the partial image areas with the nominal content, and
(ii) if the captured content corresponds to the nominal content, then confirm the determined value based on the second image analysis process.

2. The dose capturing assembly as in claim 1, further comprising:
an electronically controlled display adapted to display a set dose amount,
wherein the processor structure is adapted to:
(i) control the display to show a confirmed value, and
(ii) control the display to show an error indication if the determined value is not confirmed.

3. The dose capturing assembly as in claim 2, further comprising a sensor assembly adapted to detect rotational movement of the dose setting member, wherein the processor structure is adapted to:
(i) determine if the determined value belongs to a second pre-defined group of values, and
(ii) if the determined value belongs to the second pre-defined group of values, then turn the display into an operating state.

4. The dose capturing assembly as in claim 1, wherein the processor structure is adapted to determine an expelled dose amount based at least in part on confirmed values.

5. The dose capturing assembly as in claim 1, wherein the first image analysis process is template matching and the determined value is a rotational position of the indicator.

6. The dose capturing assembly as in claim 1, wherein the first image analysis process is an OCR process and the determined value is a numerical value corresponding to a rotational position of the indicator.

7. The dose capturing assembly as in claim 1, the dose capturing assembly being in the form of an add-on device adapted to be releasably attached to the drug delivery device.

8. A combination of the add-on device as in claim 7, and the drug delivery device, wherein the add-on device is adapted to be releasably attached to the drug delivery device.

9. The combination of the add-on device and the drug delivery device as in claim 8, wherein the drug expelling structure further comprises:
a piston rod adapted to engage and axially displace a piston in a loaded cartridge in a distal direction to thereby expel a dose of drug from the cartridge,
a rotatable drive member, and
a drive spring coupled to the drive member, the dose setting member allowing a user to simultaneously set a dose amount to be expelled and strain the drive spring correspondingly by rotation of the drive member to a set position,
wherein the strained drive spring is released to rotate the drive member to expel the set dose amount when the actuation member is actuated from the first to the second state.

10. The combination of the add-on device and the drug delivery device as in claim 8, wherein:
the indicator is in the form of an indicator member having an outer surface and being adapted to rotate relative to the housing during dose setting and dose expelling corresponding to an axis of rotation, the amount of rotation corresponding to a set dose respectively the amount of drug remaining to be expelled from a reservoir by the expelling structure, the indicator member having an initial rotational position corresponding to no dose amount being set, a pattern being arranged circumferentially or helically on the indicator member outer surface and comprising a plurality of indicia, the currently observable indicia indicating to the user the size of a currently set dose amount of drug to be expelled, and
the housing comprises a window allowing the user to observe a portion of the indicator member.

11. The combination of the add-on device and the drug delivery device as in claim 10, wherein the dose capturing assembly is adapted to capture an image of the indicator indicia.

12. The dose capturing assembly as in claim 1 formed integrally with the drug delivery device.

13. The dose capturing assembly formed integrally with the drug delivery device as in claim 12, wherein:
the indicator is in the form of a tubular indicator member having an outer surface and being adapted to rotate relative to the housing during dose setting and dose expelling corresponding to an axis of rotation, the amount of rotation corresponding to a set dose respectively, the amount of drug remaining to be expelled from a reservoir by the expelling structure, the indicator member having an initial rotational position corresponding to no dose amount being set, a pattern being arranged circumferentially or helically on the indicator member outer surface and comprising a plurality of first indicia, the currently observable first indicia indicating to the user the size of a currently set dose amount of drug to be expelled, and
the housing comprises a window allowing the user to observe a portion of the indicator member.

14. The dose capturing assembly formed integrally with the drug delivery device as in claim 13, wherein the dose capturing assembly is adapted to capture an image of the first indicia.

15. The dose capturing assembly formed integrally with the drug delivery device as in claim 13, wherein:
the tubular indicator member comprises a second surface pattern being arranged circumferentially or helically on the indicator member inner or outer surface and comprising indicia in the form of code structures, and
the dose capturing assembly is adapted to capture an image of the code structures.

* * * * *